United States Patent [19]

Bordini

[11] Patent Number: 5,173,259
[45] Date of Patent: Dec. 22, 1992

[54] STERILIZATION METHOD FOR A PACKING MACHINE THAT USES LIQUID DISINFECTANT

[75] Inventor: Giorgio Bordini, Modena, Italy

[73] Assignee: Tetra Dev-Co, Modena, Italy

[21] Appl. No.: 709,801

[22] Filed: Jun. 3, 1991

Related U.S. Application Data

[63] Continuation of Ser. No. 336,030, Apr. 11, 1989, abandoned.

[30] Foreign Application Priority Data

Apr. 27, 1988 [JP] Japan ............................... 63-107384

[51] Int. Cl.⁵ ............................ A61L 2/18; A61L 2/20
[52] U.S. Cl. ........................................ 422/28; 53/167
[58] Field of Search ........................ 53/167, 425, 426; 422/28

[56] References Cited

U.S. PATENT DOCUMENTS 4,734,268 3/1988 Redding et al. .................. 53/167 X Primary Examiner—Jill A. Johnston

[57] ABSTRACT

A sterilization method for a sterile liquid-content packing machine using liquid disinfectant for sterilizing parts of a filler pipe and connecting piping in free communication with the filler pipe requiring sterilization. A preheating heat-storage piping is provided having a capacity for holding a predetermined quantity of heat transferred to the heat piping by passing super heated air therethrough. Spray charging of a predetermined quantity of liquid disinfectant occurs for a predetermined period of time into the super heated air passing through the heat storage piping which results in vaporizing the liquid disinfectant while dropping the temperature of the mixture of vaporized disinfectant steam and super heated air due to the vaporization. The drop in the temperature of the mixture is inhibited by heat stored within the heat storage piping. The mixture is communicated within the connecting piping to be sterilized which extends from the heat storage piping. The connecting piping is at a lower temperature than the dew point temperature of the mixture without cooling the connecting piping, whereby the mixture is condensed evenly as a film of liquid disinfectant on the surfaces of inner walls thereof. A second heated air having a lower temperature relative to the super heated air is communicated into contact with the condensed liquid disinfectant for vaporizing the condensed liquid disinfectant and removing the condensed liquid disinfectant from the surfaces of the connecting piping.

26 Claims, 1 Drawing Sheet

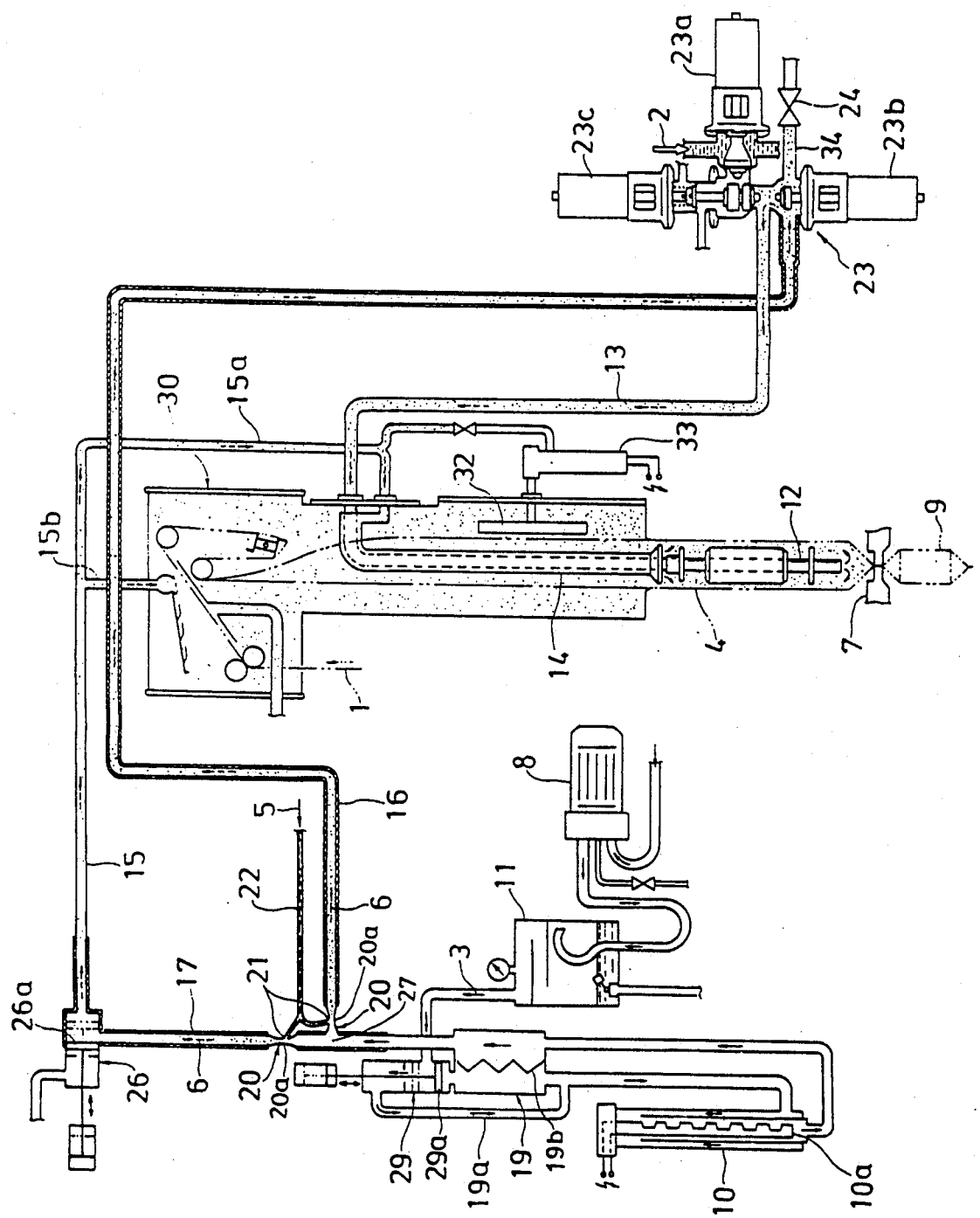

STERILIZATION METHOD FOR A PACKING MACHINE THAT USES LIQUID DISINFECTANT

This application is a continuation of application Ser. No. 07/336,030 filed on Apr. 11, 1989, now abandoned.

BACKGROUND OF THE INVENTION

1. Field of the Invention

This invention relates to a sterilization method that uses liquid disinfectant for sterilizing a filler pipe and piping in fluid communication therewith, in a sterile liquid-content packing machine.

2. Description of Background Art

In the manufacture of single-life package containers sterile-packed with liquid products such as milk or juice, web material used for packaging the contents is bent as it passes through a packing machine after sterilization. The lengthwise edges of the material slightly overlap mutually as a seal thus forming a tube, whereby the contents are supplied continuously from a filler pipe extending inward from the upper open end of the tube. As the tube travels lower, the tube is sealed as its prescribed position is pushed flat, whereby the contents level is automatically controlled so that it is sufficiently above the position where the seal is provided. Once sealed the tube separates horizontally at the sealed position, and the manufacturing process is completed after the prescribed reforming.

For a packing machine of the type described above, filling proceeds under sterilized conditions for sterile-packing manufacture. Thus, before executing filling operations at the packing machine, sterilization of the filler pipe, the piping for the product, a sterile-air inlet pipe and piping connected to the inlet to feed air so that unsterile air does not intrude from the outside of the filler pipe into contact with the upper portion of the contents in the web tube. Conventional machines sterilized the above members by use of high-temperature heated air. Recent machines sterilize with vaporized steam of hydrogen peroxide at a lower temperature to avoid the ill effects of the heat on the valve packings along the piping and web. Sterilization with hydrogen peroxide involves the spraying of liquid hydrogen peroxide, an aqueous solution of hydrogen peroxide, by opening a nozzle at a mixing chamber established along the piping that feeds heated air, and requires the production of steam. A mixture of the steam and heated air is fed to filler piping, piping, and other parts requiring sterilization. For example, in order to disinfect filler pipes and piping requiring sterilization, the method described in Japanese Patent Publication No. 53-47548, wherein the embodiment discloses the disinfecting of a web, involves disinfectant spray-mixed and vaporized with a high-temperature air stream where the mixed-air dew point has a higher temperature than the surfaces to be disinfected, so that the disinfectant cools and evenly condenses in layers over the surfaces to be disinfected. Subsequently, the disinfectant is removed. In application, the surface temperatures of parts requiring sterilization are cooled initially from the high temperatures generated from preheating operations of the packing machine, etc., followed by sterilization with a mixture of hydrogen peroxide steam and heated air.

PROBLEMS TO BE SOLVED BY THE INVENTION

In a conventional sterilization method using hydrogen peroxide to sterilize prescribed parts of a packing machine like the one described above, cooling of the parts for 10-15 minutes was required prior to sterilization so that the parts requiring sterilization had a lower temperature than the dew point of the mixture of disinfectant and air. Thus, a loss of time due to the cooling and an increase in cost which resulted were unavoidable.

The present invention takes into account the above points, and provides a sterilization method that eliminates the cooling operation where the temperature of the surfaces to be sterilized is lowered. Hence, the mixture of liquid disinfectant steam and heated air clads and condenses on the surfaces to be sterilized without cooling the surfaces. Further, an efficient vaporization method of the liquid disinfectant is provided, eliminating time loss that occurred with the use of liquid disinfectant in packing machines, improving operation efficiency, and lowering cost.

MEANS OF SOLVING THE PROBLEM

To achieve the above objectives, the sterilization method of the present invention uses piping that permits large-volume heat storage when heated air is passed through the piping. After preheating the heat-storage piping by passing high-temperature heated air through it, a large volume of liquid disinfectant is spray-charged for a prescribed time into the prescribed high-temperature heated air passing through the heat-storage piping and is vaporized. The mixture of vaporized disinfectant steam and heated air has its temperature decrease suppressed and the mixture of steam and heated air is established continually in the prescribed heat-storage piping so that without cooling the mixture contacts and passes through piping to be sterilized at a lower temperature than the dew point of the mixture. Thus, even cladding and condensing occurs on the inner surfaces of the piping and other parts requiring sterilization. Finally, heated air at a lower prescribed temperature than the high-temperature heated air noted above passes through and contacts the condensed disinfectant which is vaporized and removed.

The surface temperatures of objects to be sterilized such as the interior portion of piping at a temperature lower than the dew point of the mixture of disinfectant and heated air may be in the maximum range of 70° to 90° C., and the dew point of the mixture needs to be 90° C. or greater.

Preferably, spraying of the liquid disinfectant should work by positioning the nozzle opening next to the disinfectant supply pipe and by opening the throat of a venturi tube located in the prescribed heat-storage piping.

Also preferably, the thickness of the prescribed heat-storage piping should be a specific thickness thicker than the piping to be disinfected. In this case, establishing heat-exchanging materials such a radial fins in the thick heat-storage piping is satisfactory. Spray-charging for 15-20 seconds is satisfactory.

Moreover, hydrogen peroxide is most appropriate as the liquid disinfectant used for this device, and ordinarily obtained aqueous hydrogen peroxide solution is used.

High-temperature heated air used for preheating the prescribed heat-storage piping is exhausted from the link between the heat-storage piping and piping to be sterilized so that it does not flow to the piping to be sterilized.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawing which is given by way of illustration only, and thus, are not limitative of the present invention, and wherein:

The drawing schematically shows an embodiment of a packing machine sterilization device utilizing the sterilization method of the present invention wherein the spray-charging is in progress.

DETAILED DESCRIPTION OF THE PREFERRED EMBODIMENT

The present invention will now be described with reference to a preferred embodiment in conjunction with the accompanying drawing. The drawing schematically shows a packing machine filling device using the sterilization method of the present invention for sterilizing prescribed parts, and shows the condition during liquid disinfectant spray-charging.

To simplify the understanding of the present invention, the basic principle of liquid disinfectant sterilization methods is described for background information.

When a specific amount of liquid disinfectant is charged into heated air, as long as the air temperature is sufficiently high and higher than the condensation temperature of the air mixture of the liquid disinfectant, the air will absorb and contain the disinfectant. When the air mixture that absorbs and contains the vaporized disinfectant steam decreases in temperature below the dew point, which is the condensation temperature, the air cannot contain such a large amount of liquid, and a portion of the liquid condenses. The air temperature and ratio of liquid disinfectant volume to air volume for the air mixture containing the steam determine the dew point. Thus, contact with an object to be sterilized that is at a lower temperature than the dew point of the formed mixture causes the part of the mixture that contacts the surfaces to be cooled and the steam portion condenses and clads the surfaces with an even layer of liquid disinfectant. Later, heated air of a suitable temperature heats the surfaces and vaporizes the disinfectant to yield sterilization. The present invention efficiently sterilizes the prescribed parts of a packing machine to be sterilized based on the principle stated above.

For filling at the packing machine illustrated in the drawing, web 1 rolls off of an unillustrated roll, passes through a hydrogen peroxide bath and is sterilized. The web 1 travels above prescribed guide rollers at the top of the packing machine, is dried, and travels vertically through the packing machine toward a lower portion of the packing machine with a regulated feed. During the lower movement through the packing machine, web 1 is formed into a tube after both lengthwise edges are sealed. Into the tube material 4 thus formed, prescribed sterilized contents such as milk are filled via filler pipe 12, which extends downward near the lower edge of material tube 4 where material tube 4 ends and beyond the upper open-mouth of material tube 4. The sealing jaws 7 located a certain distance below the lower end of filler pipe 12 on both sides of material tube 4 seal said tube 4 equally horizontally while the tube 4 is filled and traveling downward vertically. The tube 4 is cut similarly horizontally and separated at the seal. The packaged object 9 thus formed is complete after prescribed reforming.

Prescribed parts of the packing machine are sterilized with liquid disinfectant prior to manufacture. Hydrogen peroxide is used as a disinfectant. The packing machine and sterilization device according to the method of the present invention that operates in conjunction with the packing machine both connect to air compressor 8, which is equipped with a water separator 11 to remove condensed water from air. Since air contains small amounts of water, the water separator 11 prevents the dilution of disinfectant when mixed with the air, and removes water to the fullest extend from the air for preheating, drying and other operations. Dry air 3 thus dehydrated is heated and used for creating hydrogen peroxide steam by vaporizing hydrogen peroxide liquid disinfectant, which is normally obtained as a 35% aqueous solution. The disinfectant is charged in the air. Means are provided for maintaining high temperatures and preventing the mixture temperature of hydrogen peroxide steam and heated air to decrease and for preheating heat-storage piping 16, 17 described later. Dehydrated air 3 emitted from the water separator travels to heat-exchanger flow transfer valve 29 via prescribed piping. According to the operating conditions of the sterilization device, a piston 29a in a transfer valve 29 switches flow paths for the spraying of hydrogen peroxide 5 and for sending heated air to heat-storage piping 16, 17 for preheating the heat-storage piping 16, 17 prior to the spraying. The transfer valve 29 sends dry air at a lower temperature than the prescribed high-temperature air to piping to be sterilized which is connected via the valve device to vaporize the hydrogen peroxide 5 liquid disinfectant from piping to be sterilized such as the inner surface of the piping. Hence, for sending high-temperature heated air to heat-storage piping 16, 17, piston 29a, which is movable up and down, is down as shown in the figure. Dehydrated air 3 emitted from water separator 11 travels to a high-temperature air heater 10 via the upper portion of a prescribed transfer valve 29 and side-path pipe 19a of a heat exchanger 19. Heater 10a of the high-temperature heater heats the air 3 to approximately 360° C. as the air passes the heater. The air 3 passes the heat exchanger 19 again and arrives at the heat-storage piping 16, 17 via a piping distribution point 27. For using heated air for drying, piston 29a moves upward in the figure, and dry air passes the interior of heat exchange 19 and travels to the high-temperature air heater 10. The high-temperature heated air passes by heat-exchanging plates 19b and is cooled by air 3 fed from water separator 11 to achieve an appropriate heated temperature, such that the air 3 feeds to piping 13, 15, which requires disinfectant to be vaporized and dried, via valves 23, 26 described later connected to heat-storage piping 16, 17. Venturi tubes are connected to the sides of both pipes 16 and 17 that communicate air from heat exchanger 19 and that lead from distribution point 27. Pipe 16, the lower pipe in the drawing, connects a filler pipe 12 of sterile production material 2 which is the liquid content to fill packaging containers, and to piping 13 connected to sterile production material valve device 23 that regulates supply to the piping 13. Pipe 17, the upper pipe in the drawing, connects to heated-air flow-path transfer valve 26, which exhausts heated air according to operating conditions or which sends heated air to piping 15, whereby sterile air is sent to the upper part of tube-shaped web 4 during filling via sterile-air inlet pipe 14, connecting piping 15a and piping 15b, connected to a sterile chamber 30.

The sterile production material valve device 23 described above consists of production material valve 23a connected to the main product-line pipe and sterile-air valve 23b that opens and closes the path of sterilizing air mixture and cleaning liquid as described later. Steam barrier valve 23c creates a sterilized steam barrier against said valve interior of main pipe described above, and switches the flow of sterile production material 2 from the product line and also switches the flow of sterile air mixture 6 from heat-storage pipe 16. Hence during production, production material valve 23a is open, sterile-air valve 23b is closed, and production material 2 enters piping 23 through the valve device. During sterilization, however, the condition is as shown in the drawing.

At the throats 20a of respective venturi tubes 20, piping 22 that conducts pressurized hydrogen peroxide 5 from an unillustrated hydrogen peroxide tank via a pump has divided ends with open nozzles 21. By movement of piston 26a, heated air-path transfer valve 26 described above switches air flow from heat-storage pipe 27 to piping 25 on the side of sterile-air feed pipe 14 or to the external side. Thus, when conducting heated air to the piping 25, piston 26a which moves to the left and right moves to the left as shown in the drawing, and when exhausting heated air the piston 26a moves to the right. Furthermore, the valve 24 is connected to sterile-air valve 23b of the prescribed sterile production material valve device 23 which is next to the pipe 34 which faces the open end of heat-storage pipe 16 and which is connected to the pipe 16. According to the operating conditions of the sterilization device, the valve 24 permits externally exhausting heated air used for preheating the heat-storage pipe 16 prior to vaporizing the hydrogen peroxide 5 in the piping 16, while the valve 24 remains closed during all times except preheating to allow the transfer of heated air flowing from the heat-storage piping 16, and the transfer of cleaning liquid from the filler pipe 12, to the piping 13. Setting the pipe wall thickness for heat-storage piping 16, 17 described above to, for example, 5 mm, permits a large volume of heat storage by increasing the heat capacity of the heat-storage piping. The drawing indicates pipe walls as cross sections, and thick walls are established slightly before distribution point 27. Hot air nozzles 32 are located low in the sterilization chamber for vertically sealing the two length wise edges of the tube-shaped web 4 by heating and fusing. An air heater 33 is used to send heated air to hot-air nozzles 32.

The following describes sterilization of the packing machine filling section by hydrogen peroxide 5 liquid disinfectant. The drawing shows the condition for sterilizing the prescribed parts by creating a mixture 6 of hydrogen peroxide steam and heated air by spray-charging hydrogen peroxide into heat-storage piping 16, 17. The hydrogen peroxide 5, ordinarily obtained as an aqueous solution, is a mixture of hydrogen peroxide ($H_2O_2$). The most appropriate solution is a concentration of 35%. Prior to sterilization with the hydrogen peroxide 5, the heat-storage piping 16, 17 is preheated with high-temperature heated air. In other words, air is compressed with air compressor 8 and water is separated with water separator 11 to yield dehydrated air 3 which enters the heat-exchanger flow-path switching valve 29. The air 3 then enters from above the valve into high-temperature air heater 10 via side pipe 19a, and is heated by the heated and engaged heater 10a.

The high-temperature heated air at approximately 360° C. travels through the heat exchanger without exchange of heat to flow distribution point 27. During preheating prior to spray-charging hydrogen peroxide 5, from the distribution point 27 to the side of heat-storage pipe 16 of filler pipe 12 and to the other side of sterile-air inlet pipe 14 and sterile chamber 30, ⅔ of the flow volume of the high-temperature heated air described above is sent to the former side of heat-storage pipe 16 and ⅓ of the flow volume of said heated air is sent to the latter side of heat-storage pipe 17. This enables efficient preheating of the prescribed parts for hydrogen peroxide sterilization. High-temperature heated air that passes distribution point 27 and flows into heat-storage pipe 16 on the filler-pipe side and into heat-storage pipe 17 on the other side heats the pipe walls for a prescribed period 15 to 20 seconds. The air that flowed into the heat-storage pipe 16 on the filler-pipe side passes sterile-air valve 23b of sterile production material valve device 23, and is exhausted from valve 24 on pipe 34 which is only open during preheating. At this time, sterile-air valve 23b of sterile production material valve device 23 has moved, upward from the condition in the drawing, and is closed so that high-temperature heated air does not enter piping 13 connected to filler pipe 12. Steam barrier valve 23c and production material valve 23a remain in the condition shown in the drawing so that the flow of sterile production material 2 to the filler-pipe side is stopped, and sterile steam fills the interior of the steam barrier valve 23c. The high-temperature heated air that flowed into the heat-storage pipe 17 to heat the pipe walls is exhausted externally by moving heated-air flow-path transfer valve 26a to the left, shown in dotted lines, because the piston is moved to the right during preheating. In this way, because high-temperature heated air does not flow to the filler pipe 12 and the connecting piping 13, sterile-air feed pipe 14 and connecting piping 15, 15a, and piping 15b connected to the upper part of sterilization chamber 30, temperature increase in parts requiring sterilization is completely prevented so that internal machine temperature, a maximum of 70° to 90° C., is maintained for operations prior to preheating described above such as preheating vertically sealing hot-air nozzles 32.

After preheating for the prescribed period and after a sufficiently large heat storage takes place within heat-storage piping 16, 17, high-temperature heated air is sent continuously to the heat-storage piping 16, 17. Then, in a pressurized condition, hydrogen peroxide 5, aqueous solution, which is a mixture of at least 35% hydrogen peroxide ($H_2O_2$) and water is sent from an unillustrated hydrogen peroxide tank by a pump via piping 22 to the divided nozzles 21, and spray-charged into high-temperature heated air passing through the venturi tubes 20 which are established on heat-storage piping 16, 17. A spraying time of 15 to 20 seconds is suitable, with an upper limit of 40 to 50 seconds permissible. Because nozzle openings are located at the throats 20a of venturi tubes 20, the high-temperature heated air passing the venturi tubes 20 increases its flow speed at the throats 20a and pressure decreases while heat is restored from wall surfaces of heat-storage piping 16, 17 to the hydrogen peroxide sprayed as a mist, causing instant vaporization. During spraying, heated air temperature changes from 320° C., spray started, to 200° C., spray ended. In addition, by establishing radial fins in the heat-storage piping 16, 17 described above, vaporization is made efficient without worry of recondensation because heat transfer from the heat-storage piping 16, 17 is facilitated. The vaporized hydrogen peroxide steam mixes with the high-temperature air flow and becomes a mixture 6 of hydrogen peroxide and air. Due to the absorption of the heat of vaporization during vaporization, the temperature of the mixture 6 attempts to greatly decrease, but instead is restored with a large volume of heat as it passes through heat-storage piping 16, 17, attaining a temperature relatively higher than when the dew point of mixture 6 is not restored with heat, whereby the mixture 6 traveling along the heat-storage pipe 16 is communicated with the filler pipe 12 via piping 13 to be sterilized and via sterile production material valve device 23. The mixture 6 traveling along the heat-storage pipe 17 is conducted through the high-temperature air flow-path transfer valve 26, in this case valve plug 26a of the valve 26 is to the left as shown in the drawing, and from the piping 15 in part to sterile-air inlet pipe 14 in a tube-shaped web 4 via piping 15a and in part to within the sterilization chamber 30 from the upper portion of the chamber 30 via the piping 15b.

At this time, because surface temperatures of the piping to be sterilized 13, 15, 15a, 15b, filler pipe 12, and inner surfaces of the sterile-air inlet pipe 14, the sterile-air inlet pipe 14 inside sterilization chamber 30, and the outer surfaces of the filler pipe 12 remain within the maximum range of 70° to 90° C. around the heat source for the vertically sealing hot-air nozzles 32, special cooling operations, ordinarily 10 to 15 minutes, are not required. The hydrogen peroxide steam in the mixture described above clads and condenses as a thin layer on the surfaces to be sterilized which are below the dew point of the mixture described above. Valve 24 on pipe 34 connected to sterile-air valve 23b of the sterile production material valve device is closed during the above operation. After the appropriate time passes, heated air of a prescribed temperature which is lower than the high-temperature heated air described above, to avoid the ill effects of high temperature on the packing of the filler pipe, etc., is used to evaporate the clad film of hydrogen peroxide disinfectant and to complete sterilization. Hence, in this case, piston 29a of heat-exchanging flow-path transfer valve 29 is moved upwardly as shown with dotted lines, and dehydrated air 3 emitted from water separator 11 enters the flow-path transfer valve 29 and travels through the heat exchanger 19 from the lower part of the valve 29 to the high-temperature air heater 10. The high-temperature heated air passes through heat exchanger 19 again, but is cooled via heat-exchanging plates 19b by dehydrated air 3 flowing into heat exchanger 19. As heated air at a lower temperature than the high-temperature heated air for hydrogen peroxide spray-charging, the air is sent to piping and filler piping to be sterilized from piping distribution point 27 as described previously for sterilizing and drying hydrogen peroxide 5 condensed and clad to the surfaces to be sterilized. Evaporated hydrogen peroxide is exhausted along with heated air from the packing machine. During this time, the heated air temperature changes from an initial 200° C. to 130° C. after vaporization and drying. In this case, surfaces to be sterilized are not cooled so the initial temperature is higher for excellent drying, and residual amounts of hydrogen peroxide can be held to a minimum at production time.

In the manufacture of single-life packaging containers for the sterile-packing of liquid beverages such as milk, prior to the introduction of sterile liquid contents from the main product line pipe via a regulating flow valve device, recently improved sterilizing systems have incorporated hydrogen peroxide steam for the sterilization of filler piping of contents and other parts to be sterilized. The prior devices required the initial cooling of surfaces to be sterilized. Hence, time loss and a resulting increase in costs were unavoidable. By adopting the method of the present invention, highly concentrated conditions permit the generation of disinfectant steam such as hydrogen peroxide to provide superior condensation on the surfaces to be sterilized. All cooling operations for the surfaces to be sterilized can be eliminated for increased operating efficiency and decreased costs. Further, because cooling operations on the surfaces to be sterilized are not required, good drying takes place which minimizes residual amounts of disinfectant for safer sterilization operations.

Establishing a maximum surface temperature range of 70° to 90° C. is a suitable temperature for eliminating cooling operations, and by establishing a dew point of 90° C. or greater for the mixture of air and liquid disinfectant, sterilization operations without cooling the surfaces to be sterilized and thus with less work can be carried out smoothly.

In addition, rapid vaporization occurs by opening nozzle openings at the throats of the venturi tubes in the heat-storage piping. Further, by making the pipe walls thick in the heat-storage piping a large amount of heat storage is facilitated and this is effective for raising the dew point of the mixture of air and disinfectant. Establishing heat-exchanging parts such as radial fins efficiently raises the dew point of the mixture described above.

Moreover, by setting the spray-charging time for liquid disinfectant to 15 to 20 seconds, efficient sterilization operations can be carried out without waste at the packing machine. Liquid disinfectant such as hydrogen peroxide is most suitable for sterilization.

In the execution of the method described above, by externally exhausting the heated air used for preheating heat-storage piping at the link between the heat-storage piping and piping to be sterilized, the temperature rise of surfaces to be sterilized is completely prevented, for efficient condensation of liquid disinfectant on the surfaces to be sterilized or disinfected.

OPERATION OF THE INVENTION

With the sterilization method of the present invention arranged as described above, the heat-storage piping to be preheated stores a large volume of heat by passing high-temperature heated air. Thus, when a large amount of liquid disinfectant is spray-charged for a prescribed time into the flow of high-temperature heated air in the heat-storage piping, the liquid disinfectant vaporizes and becomes steam whereby the heat of water vaporization is absorbed so that the mixture of liquid-disinfectant steam and heated air attempts to significantly decrease in temperature. However, the heat of vaporization is restored by the heat stored in the heat-storage piping at vaporization via the interior walls of the piping, and temperature decrease is suppressed. For this reason, a dew-point decrease of the mixture, which fluctuates according to the air temperature and the ratio of disinfectant volume to air volume, is prevented. The dew point rises compared to when heat of vaporization is not restored from heat-storage piping walls. When the mixture is continually established and contacts sterilizing objects such as piping to be sterilized as it passes, the objects are ordinarily at a lower temperature than the dew point of the mixture so the mixture cools on the surfaces of the parts requiring sterilization such as the inner surfaces of the piping whereby the disinfectant steam condenses and forms an even cladding on the surfaces. Later heated air of a prescribed temperature passes and contacts the condensed disinfectant which then evaporates and is removed, and the surfaces are sterilized.

If surface temperatures of the interiors of the piping, etc., to be sterilized are in the maximum range of 70° to 90° C., this permits packing machines to ordinarily stand without cooling. If the dew point of the mixture in this case is 90° C. or greater, disinfectant can be condensed smoothly on surfaces to be sterilized.

In addition, when spray-charging liquid disinfectant, vaporization proceeds rapidly by opening the throat of a venturi tube established in the heat-storage piping, since the flow speed of heated air increases and inner pressure decreases at the venturi tube throat.

Moreover, by increasing the piping wall thickness of the heat-storage piping thicker than the ordinary piping to be sterilized, the heat capacity becomes large and heat-storage capacity increases. Thus, it is easy to prevent dew-point decrease of the mixture of disinfectant and heated air. The heat transfer toward the mixture is made efficient and fast by establishing heat-exchanging material such as radial fins in the heat-storage piping described above. Spray-charging for 15 to 20 seconds also permits efficient operation.

When preheating the heat-storage piping described above, the high-temperature heated air used is exhausted from the link between the heat-storage piping and piping to be sterilized, and completely prevents the temperature of the piping to be sterilized to rise.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A sterilization method for a sterile liquid content packing machine using liquid disinfectant for sterilizing parts of a filler pipe and connecting piping in free communication with the filler pipe requiring sterilization comprising the following steps:
    preheating heat-storage piping having a capacity for holding a predetermined quantity of heat transferred to the heat storage piping by passing a first stream of super heated air therethrough;
    spray charging a predetermined quantity of liquid disinfectant for a predetermined period of time in the super heated air passing through the heat-storage piping and vaporizing said liquid disinfectant while inhibiting a drop in temperature of the mixture of vaporized disinfectant steam and super heated air due to the vaporization by heat stored within the heat-storage piping;
    communicating the mixture within the connecting piping to be sterilized extending from the heat-storage piping, said connecting piping being at a lower temperature than the dew point temperature of the mixture without cooling said connecting piping, whereby the mixture is condensed evenly as a film of liquid disinfectant on the surfaces of inner walls thereof; and
    communicating a second stream of heated air having a lower temperature relative to the super heated air into contact with said liquid disinfectant for vaporizing the condensed liquid disinfectant and removing the condensed liquid disinfectant from the surfaces of the connecting piping;
    wherein the thickness of the heat-storage piping is of a predetermined thickness being thicker relative tot he thickness of the connecting piping extending from the heat-storage piping.

2. The sterilization method using liquid disinfectant for sterilization a packing machine according to claim 1, wherein the maximum surface temperature of the interior portions of the connecting piping to be sterilized is at a lower temperature than the dew point temperature of the mixture of disinfectant and super heated air and being in the range of 70 to 90 degrees centigrade.

3. The sterilization method using liquid disinfectant for sterilizing a packing machine according to claim 2, wherein the spraying of liquid disinfectant into the heat-storage piping includes a nozzle opening of a disinfectant supply pipe open to a throat portion of a venturi tube located in the heat-storage piping.

4. The sterilization method using liquid disinfectant for sterilizing a packing machine according to claim 3, wherein said spraying is conducted for 15 to 20 seconds.

5. The sterilization method using liquid disinfectant for sterilizing a packing machine according to claim 3, wherein said liquid disinfectant is hydrogen peroxide.

6. The sterilization method using liquid disinfectant for sterilizing a packing machine according to claim 2, wherein the thickness of the heat-storage piping is of a predetermined thickness being thicker relative to the thickness of the connecting piping extending from the heat-storage piping.

7. The sterilization method using liquid disinfectant for sterilizing a packing machine according to claim 6, wherein the heat-storage piping includes heat exchanging radial fins.

8. The sterilization method using liquid disinfectant for sterilizing a packing machine according to claim 2, wherein said spraying is conducted for 15 to 20 seconds.

9. The sterilization method using liquid disinfectant for sterilizing a packing machine according to claim 2, wherein said liquid disinfectant is hydrogen peroxide.

10. The sterilization method using liquid disinfectant for sterilizing a packing machine according to claim 2, further comprising the step of exhausting the super heated air from a connecting portion of the heat-storage piping and connecting piping to be sterilized after preheating of the connecting piping.

11. The sterilization method using liquid disinfectant for sterilizing a packing machine according to claim 2, wherein the dew point temperature of the mixture of disinfectant and super heated air is higher than 90 degrees centigrade.

12. The sterilization method using liquid disinfectant for sterilizing a packing machine according to claim 11, wherein the spraying of liquid disinfectant into the heat-storage piping includes a nozzle opening of a disinfectant supply pipe open to a throat portion of a venturi tube located in the heat-storage piping.

13. The sterilization method using liquid disinfectant for sterilizing a packing machine according to claim 11, wherein said spraying is conducted for 15 to 20 seconds.

14. The sterilization method using liquid disinfectant for sterilizing a packing machine according to claim 12, wherein said spraying is conducted for 15 to 20 seconds.

15. The sterilization method using liquid disinfectant for sterilizing a packing machine according to claim 11, wherein said liquid disinfectant is hydrogen peroxide.

16. The sterilization method using liquid disinfectant for sterilizing a packing machine according to claim 12, wherein said liquid disinfectant is hydrogen peroxide.

17. The sterilization method using liquid disinfectant for sterilizing a packing machine according to claim 11, further comprising the step of exhausting the super heated air from a connecting portion of the heat-storage piping and connecting piping to be sterilized after preheating of the connecting piping.

18. The sterilization method using liquid disinfectant for sterilizing a packing machine according to claim 1, wherein the spraying of liquid disinfectant into the heat-storage piping includes a nozzle opening of a disinfectant supply pipe open to a throat portion of a venturi tube located in the heat-storage piping.

19. The sterilization method using liquid disinfectant for sterilizing a packing machine according to claim 18, wherein the thickness of the heat-storage piping is of a predetermined thickness being thicker relative to the thickness of the connecting piping extending from the heat-storage piping.

20. The sterilization method using liquid disinfectant for sterilizing a packing machine according to claim 19, wherein the heat-storage piping includes heat exchanging radial fins.

21. The sterilization method using liquid disinfectant for sterilizing a packing machine according to claim 18, wherein said spraying is conducted for 15 to 20 seconds.

22. The sterilization method using liquid disinfectant for sterilizing a packing machine according to claim 18, wherein said liquid disinfectant is hydrogen peroxide.

23. The sterilization method using liquid disinfectant for sterilizing a packing method according to claim 1, wherein the heat-storage piping includes heat exchanging radial fins.

24. The sterilization method using liquid disinfectant for sterilizing a packing machine according to claim 1, wherein said spraying is conducted for 15 to 20 seconds.

25. The sterilization method using liquid disinfectant for sterilizing a packing machine according to claim 1, wherein said liquid disinfectant is hydrogen peroxide.

26. The sterilization method using liquid disinfectant for sterilizing a packing machine according to claim 1, further comprising the step of exhausting the super heated air from a connecting portion of the heat-storage piping and connecting piping to be sterilized after preheating of the connecting piping.

* * * * *